United States Patent [19]
Moller et al.

[11] Patent Number: 5,410,025
[45] Date of Patent: Apr. 25, 1995

[54] UNMODIFIED INTRAVENOUSLY ADMINISTERED IMMUNOGLOBULIN PREPARATIONS CONTAINING IMMUNOGLOBULIN M AND/OR A

[75] Inventors: Wolfgang Moller, Oberursel; Detlef Piechaczek, Munster, both of Germany

[73] Assignee: Biotest Pharma GmbH, Dreieich, Germany

[21] Appl. No.: 154,149

[22] Filed: Nov. 18, 1993

Related U.S. Application Data

[63] Continuation of Ser. No. 782,747, Oct. 18, 1991, abandoned, which is a continuation of Ser. No. 561,037, Aug. 1, 1990, abandoned.

[30] Foreign Application Priority Data

Aug. 17, 1989 [DE] Germany .................. 39 27 111.0

[51] Int. Cl.$^6$ .................. A61K 35/14; C07K 3/12
[52] U.S. Cl. .................. 530/390.5; 530/387.1; 530/412; 530/416
[58] Field of Search .................. 530/389.1, 368, 369, 530/387.1, 412, 416, 390.5

[56] References Cited

U.S. PATENT DOCUMENTS

| | | | |
|---|---|---|---|
| 3,808,189 | 4/1974 | Breuer. | |
| 4,613,501 | 9/1986 | Horowitz | 424/89 |
| 4,877,866 | 10/1989 | Rudnick et al. | 530/387 |
| 5,159,064 | 10/1992 | Mitea et al. | 530/388.1 |

OTHER PUBLICATIONS

Ion Exchange Chromatography, Principles and Methods.
Jawetz et al., Review of Medical Microbiology, p. 350, 1984.
Goding et al., Monoclonial Antibodies: Principles and Practice, pp. 112–116, 1986.
Kabat et al., Experimental Immunochemistry, p. 211, 1961.
Arzneimittel-Forschung Drug Research, 1985, pp. 2–11.
Pentaglobin, Human Immunoglobulin Containing Ig/VI for Intravenous Drug Use Against Bacterial Organisms.
Pentaglobin, The Chance to Survive Septic Shock. DMW 1987, 112.Jg., Nr. 33, 1267–1271.
Intensivmedizin und Notfallimedizin 24 (6), 314 (1987).
Noack, et al., Intravenous immunoglobulin M in the treatment of infants with septicaemia and bacterial meningitis.
Thrombosis and Haemostasis, THHADQ 58(1) 1–676 (1987) Jul. 6, 1987.
2. Wiener Schockgesprache, May 11–14, 1988.
Journal of Obstetrics and Gynaecology (1989) 10. (Suppl 1) S 25 S26.
Abstracts, SY 82, Use of an IgM Enriched Intravenous Immunoglobulin in Bone Marrow Transplantation, C. H. Poynton, Cardiff, Wales.
Abstracts, Protection of infection-prone cardiopulmonary bypass patients by postoperative immunoglobulin prophylaxis, H. G. Kress, Wurzburg, FRG.
Critical Care Medicine, 1991, vol. 19, No. 9, Treatment of Gram-negative septic shock with an immunoglobulin preparation.
W. Stephan, Investigations to Demonstrate the Antibacterial and Antitoxic Efficacy of an IgM-Enriched Intravenous Immunoglobulin Preparation; Immune Consequences of Trauma; 1989.
Hood et al., Immunology, 1984, pp. 84–87.
Johnstone et al., Immunochemistry in Practice, 1987, pp. 72–77.
Roitt et al., 1989, Immunology, p. 57, Fig. 5.18.
Chen et al., T. Chromatography, vol. 444 pp. 153–164 (1988).

*Primary Examiner*—David L. Lacey
*Assistant Examiner*—F. C. Eisenschenh
*Attorney, Agent, or Firm*—Sprung Horn Kramer & Woods

[57] ABSTRACT

Intravenously administered chemically unmodified immunoglobulin preparation containing more than 5% of its total immunoglobulin by weight consisting of IgM and/or more than 10% of its total immunoglobulin of IgA and with a low anticomplementary activity, and method of preparing it by anion-exchange chromatography.

8 Claims, No Drawings

UNMODIFIED INTRAVENOUSLY ADMINISTERED IMMUNOGLOBULIN PREPARATIONS CONTAINING IMMUNOGLOBULIN M AND/OR A

This application is a continuation, of application Ser. No. 782,747, filed Sep. 18, 1991, now abandoned which is a continuation of application Ser. No. 561,037, filed Aug. 1, 1990, now abandoned.

The present invention relates to intravenously compatible immunoglobulin preparations that have not been chemically modified and that contain more than 5% immunoglobulin M (IgM) and/or more than 10% immunoglobulin A (IgA) in terms of their total immunoglobulin content.

The immunoglobulins are a group of glycoproteins that occur in the body in response to the appearance of foreign antigens and are responsible for attacking and eliminating them. Although there are several classes of immunoglobulins, only IgG, IgA, and IgM occur in the plasma in significant concentrations.

At approximately 12 mg/ml, IgG is the major immunoglobulin in the plasma. It is mainly responsible for combating viral infections. The concentration of IgM is definitely lower—approximately 1.5 mg/ml. IgM is mainly involved in combating bacterial pathogens and in picking up bacterial toxins. IgA has a mean plasma concentration of 3.5 mg/ml, has the responsibility of neutralizing various viruses, those of poliomyelitis, measles, and influenza for example, and is encountered in its secretory, dimeric form in the seromucous secretions.

Immunoglobulin preparations have been employed for passive immunotherapy for some 40 years. Most of these substances are pure IgG preparations, with only low levels of IgA and IgM. Immunoglobulin preparations, furthermore, could be administered only intramuscularly prior to the 1960's, and their painful side effects prevented the use of large doses.

Several intravenously applicable IgG preparations were subsequently developed either by modifying the immunoglobulin chemically or enzymatically or by other methods.

IgG preparations, however, that also contained significant levels of IgM and/or IgA—those described in German Patent 2 404 265 or U.S. Pat. No. 3 808 189 for example—were still applicable only intramuscularly.

The first and up to now only intravenously applicable immunoglobulins to contain IgM and/or IgA are described in European Patent 0 013 901 and in German OS 3 825 429. Both of these preparations are essentially rendered intravenously applicable by being chemically modified with β-propiolactone (BPL). One measure of the intravenous compatibility of immunoglobulin preparation is the anticomplementary activity (ACA) described by E. Kabat and M. Mayer in Experimental Immunochemistry, 2nd ed., 1964, Springfield, Ill., Thomas Brooks, 133-240.

The object of the present invention is to develop immunoglobulin preparations that contain IgM and/or IgA, that have a low anticomplementary activity, and that are intravenously applicable although not chemically modified.

This object is attained by treating an immunoglobulin solution that contains immunoglobulin M and/or immunoglobulin A with an anion exchanger, gradient-eluting a fraction with a low anticomplementary activity, and optionally subjecting the fraction to a brief treatment at low pH and/or high temperature.

It has been surprisingly discovered that anion-exchange chromatography will attach the fraction responsible for the high anticomplementary activity so securely that subsequent elution under appropriate condition will wash out approximately 95% of the immunoglobulins collected, including most if the IgM and IgA with a low anticomplementary activity.

If the starting material has an elevated anticomplementary activity, the additional brief treatment of the eluate at low pH and/or high temperature will lower it to a level that is normal for intravenously applicable products.

Also surprising was the discovery that using a starting material with a low anticomplementary activity will sometimes make it possible to lower the anticomplementary activity just by treating the eluate from the anion exchanger at a low pH and/or high temperature with no need to remove some of the IgA and IgM through chromatography.

It will be obvious that the starting material for the anion-exchange chromatography should be produced under conditions that will protect the protein as much as possible against denaturation. Appropriate starting materials are solutions that contain immunoglobulin—Cohn Fraction II/III or Cohn Fraction III, other plasma fractions that contain IgA or IgM, such other solutions as milk or milk fractions, other body fluids, or residues from cultures of cells that produce IgA and/or IgM for example.

A fraction—Cohn Fraction II/III or III for example—that contains immunoglobulin can for example be dissolved in a buffer, and most of the impurities eliminated by precipitation with 0.5 to 5% octanoic acid at a pH of 4 to 6 and preferably 5. The solution is then treated at a low conductivity with an anion exchanger, attaching most of the IgA and IgM. Adsorption can be carried out batchwise, in a chromatography column, or on membranes.

If the desired product is to contain IgA and IgM the elution is carried out with a salt gradient that will leave approximately 10 to 20% of the IgM on the matrix. The precise eluting conditions depend on the type of anion exchanger and range from 10 to 400 $m_{osm}$, depending on the matrix and pH. The specifications for specific matrices are cited in the examples.

If the product is intended to contain IgA and not IgM, the elution is carried out at a lower osmolarity and the IgM will remain adsorbed onto the matrix. Depending on the chromatographic conditions, the eluate will contain 30 to 60% IgA and 70 to 40% IgG. The IgA can be further purified by appropriate measures.

If on the other hand the eluate also contains significant levels of IgM, the anticomplementary activity can be further decreased by 1 minute to 24 hours of additional treatment at a low pH, preferably 4 to 4.5, and/or at a higher temperature, 40° to 60° C. and preferably 50° to 54° C.

A pure IgM solution, extensively free of IgA, can be obtained by washing the anion exchanger ahead of time with a buffer to elute the IgA before the IgM.

When the anticomplementary activity in the starting material is lower, all of the IgM fraction that is adsorbed onto the anion exchanger can sometimes be eluted. In this situation, treating the eluate for 1 minute to 4 hours at a low pH, preferably 4 to 4.5, and/or at a high temperature, 40° to 60° C. and preferably 50° to 54°

C., will be sufficient by itself to reduce the activity to a tolerable level.

The solution can then be concentrated by ultrafiltration and its electrolyte level adjusted to that of the final intravenous formulation by diafiltration. The anticomplementary activity of the final product will then be in the range conventional for common commercial intravenous-IgG preparations or for the chemically modified IgM preparation Pentaglobin.

Since the anticomplementary activity of the IgG fraction not attached to the anion exchanger is also very low, the fraction can be employed in conjunction with the fractions that contain IgA and/or IgM in accordance with the invention to prepare mixtures that can be converted into intravenously compatible immunoglobulin preparations with a low anticomplementary activity and a desired ratio of IgG, IgA, and IgM. An immunoglobulin preparation that contains IgM and IgA and has the same composition as the commercial, chemically modified Pentaglobin—80% IgG, 10% IgA, and 10% IgM—for example but with an anticomplementary activity that is equal or lower can be prepared.

The immunoglobulin preparations that contain IgM and/or IgA in accordance with the invention can be subjected before or after the steps of the method in accordance with the invention to such in-themselves known sterilization procedures as treatment with β-propiolactone and ultraviolet light, treatment with solvents and/or detergents, or pasteurization.

The invention will now be described with reference to examples without being limited to them.

EXAMPLE 1

10 kg of Cohn paste III were dissolved in 50 l of 0.1M acetate buffer at a pH of 5 and treated with 1.5 kg of octanoic acid. The precipitate was centrifuged out after 4 hours and the supernatant dialyzed against 20 mM of piperazine and 20 mM of sodium chloride at a pH of 6. The solution is then applied onto a 5-l column of TMAE-Fraktogel (Merck, Darmstadt) equilibrated with the same buffer and chromatographed in 5 runs. The unattached IgG fraction was collected and concentrated by ultrafiltration.

An IgA-rich fraction was eluted with 20 mM of piperazine and 100 mM of sodium chloride at a pH of 6 and an IgM-rich fraction with 20 mM of piperazine and 150 mM of sodium chloride at a pH of 6. The rest of the attached protein was then washed out of the column with 20 mM of piperazine and 190 mM of sodium chloride at a pH of 6.

Table 1 shows the fraction's composition and anticomplementary activity,

TABLE 1

|  | IgG g/l | IgA g/l | IgM g/l | ACA CH 50/ml |
|---|---|---|---|---|
| IgG fraction | 50 | 0.3 | 0 | 9 |
| IgA fraction | 31 | 18 | 0.1 | 17 |
| IgM fraction | 9 | 9 | 31 | 41 |
| residual fraction | 8 | 3 | 39 | 441 |

A chemically unmodified immunoglobulin preparation comprising 80% IgG, 10% IgA, and 10% IgM was then mixed from the IgG, IgA, and IgM fractions in this example and compared with the commercial product Pentaglobin, which is modified with β-propiolactone (Table 2).

TABLE 2

|  | IgG g/l | IgA g/l | IgM g/l | ACA CH 50/ml |
|---|---|---|---|---|
| Invention preparation: | 40.0 | 4.9 | 5.0 | 13 |
| Pentaglobin, Batch 1462019 (reference): | 43.4 | 4.2 | 5.0 | 26 |

EXAMPLE 2

1 kg of Cohn Paste III was treated as described in Example 1. It was applied onto a chromatography column and immediately eluted with 20 mM of piperazine and 160 mM of sodium chloride at a pH of 6. The fraction contained 50% IgG, 23% IgA, and 27% IgM in terms of the overall immunoglobulin content. The anticomplementary activity was 26 CH 50/ml.

EXAMPLE 3

1 kg of Cohn Paste III was treated as described in Example 1 and passed in two runs through a 2 l column of QMA-Accell. It was immediately eluted with 20 mM of piperazine and 20 mM of sodium chloride at a pH of 4.7. The fraction contained 38% IgG, 27% IgA, and 35% IgM in terms of the overall immunoglobulin content. The anticomplementary activity was CH 50/ml and decreased to 20 CH 50/ml subsequent to 30 minutes of treatment at a pH of 4.0.

EXAMPLE 4

10 kg of Cohn Paste II/III were treated as described in Example 1. Since Paste II/III contains more IgG than Paste III does, the level of octanoic acid was decreased to 0.75 kg. Table 3 illustrates the properties of the eluates.

TABLE 3

|  | IgG g/l | IgA g/l | IgM g/l | ACA CH 50/ml |
|---|---|---|---|---|
| IgG fraction | 49 | 1 | 0 | 4 |
| IgA fraction | 35 | 15 | 0.2 | 7 |
| IgM fraction | 9 | 10 | 3.0 | 19 |
| Remaining fraction | 10 | 4 | 36 | 193 |

EXAMPLE 5

1 kg of Cohn Paste III was treated as described in Example 1. It was applied onto the chromatography column, washed with 20 of piperazine and 120 mM of sodium chloride at a pH of 6, and eluted with 20 mM of piperazine and 175 mM of sodium chloride at a pH of 6. The eluate was concentrated by ultrafiltration and adjusted by diafiltration to a protein level of 50 g/l in 75 mM of sodium chloride and 2.5% glucose at a pH of 7. Table 4 illustrates the preparation's properties.

TABLE 4

|  | Protein g/l | IgM g/l | ACA CH 50/ml | Rec. Titer[2] Ps. aerug. |
|---|---|---|---|---|
| IgM preparation (invention) |  |  |  |  |
| After chromatography | 54.3 | 50.5 | 2300 | 40 960 |
| After 20 min. @ 50° C. | 54.3 | 50.5 | 29 | 40 960 |
| After freeze-drying[1] | 50.7 | 46.5 | 27 | 40 960 |
| Pentaglobin |  |  |  |  |
| Batch 1462019 | 53.3 | 5.0 | 26 | 1 280 |

TABLE 4-continued

|  | Protein g/l | IgM g/l | ACA CH 50/ml | Rec. Titer[2] Ps. aerug. |
|---|---|---|---|---|
| (reference) | | | | |

[1]Reconstituted with distilled water.
[2]The antibacterial titer against Pseudomonas aeruginosa was determined by passive hemagglutination as described by E. Neter, Bact. Rev. 20, 166 (1956).

EXAMPLE 6

6 kg of Cohn Paste III were treated as described in Example 1. It was applied onto a chromatography column, washed at each of 3 runs with 20 mM of piperazine and 120 mM of sodium chloride at a pH of 6, and eluted with 20 mM of piperazine and 175 mM of sodium chloride at a pH of 6. The three IgM eluates were combined, and 3 l of the resulting 12 were treated as described in Example 5.

The other 9 l were irradiated in a rotary-circulation apparatus with two 20 W ultraviolet lamps at 600 rpm and a throughput of 20 l per hour at a distance of 1 cm.

Subsequent to concentration to 40 g of protein/l by ultrafiltration, half of the solution was treated with 0.05% β-propiolactone for 90 minutes at a pH of 7.2 and a temperature of 25° C.

The other half of the solution was treated for 4 hours at 25° C. with 0.3% tri-N-butyl phosphate (TNBP) and 1% Tween 80. Both batches were then treated as described in Example 5.

The two preparations were adjusted to the same protein and IgM contents. Table 5 illustrates the anticomplementary activity and the antibacterial titer.

TABLE 5

|  | ACA CH 50/ml | Rec. Titer Pseudomonas aeruginosa |
|---|---|---|
| Unsterilized | 32 | 20 480 |
| Sterilized with UV & BPL | 30 | 20 480 |
| Sterilized with UV, TNBP, and Tween | 31 | 20 480 |

Subject to the conditions acceptable for adequate inactivation of human-pathogenic viruses, neither the anticomplementary activity nor the antibacterial action of the IgM preparation altered significantly.

The immunoglobulin preparations in accordance with the invention, which can be made available as is or optionally in the form of solutions that must be diluted before injection or freeze-dried, can also contain additional proteins (human albumin for example), sugars (glucose for example), amino acids, or appropriate monoclonal antibodies.

It will be appreciated that the instant specification and claims are set forth by way of illustration and not limitation, and that various modifications and changes may be made without departing from the spirit and scope of the present invention.

We claim:

1. A process for preparing a polyclonal chemically unmodified immunoglobulin preparation wherein at least 5% by weight of all the immunoglobulin it contains is IgM, which is low in anticomplementary activity, and which is directly adminstrable intravenously, from polyclonal material which is either a chemically unmodified human Cohn fraction II/III or a chemically unmodified human Cohn fraction III that contains immunoglobulins which comprises passing the polyclonal material through an anion exchange column under conditions to absorb the immunoglobulins to the column, passing through said column an eluant, wherein said eluant comprises a sodium chloride gradient with a concentration of 20 mM to 175 mM and a buffer under acidic conditions, such that high anticomplementary activity immunoglobulins remain bound to the column while low anticomplemetary immunoglobulins are selectively eluted, and collecting the eluate containing said low anticomplementary immunoglobulins.

2. The method according to claim 1, wherein the initial polyclonal material or the eluate is heated to 40° to 60° C. for 1 minute to 24 hours.

3. The method according to claim 1, wherein the initial polyclonal material or the eluate is incubated at a pH of 3.5 to 5 for 1 minute to 24 hours.

4. The method according to claim 1, wherein the anion exchanger is a polymer with a TMAE (trimethyl amino ethyl) group or a QMA (quarternary amino ethyl) group.

5. The method according to claim 1, wherein the anion exchanger is a polymer with a DEAE (diethyl amino ethyl) group.

6. The method according to claim 1, wherein the buffer comprises 20 mM of piperazine.

7. The method according to claim 1, wherein the eluant has a pH in the range of 4.7 to 6.

8. The method according to claim 1, wherein the anion exchanger is a member selected from the group consisting of
   a) a copolymer of the primary monomer N-Acryloyl-2-amino-2-hydroxy-methyl-1,3-propandiol and a trimethylaminoethyl-derivative of the monomer, and
   b) a natural polysaccharide with quaternary amino groups.

* * * * *